United States Patent [19]

Sherman

[11] 4,143,654
[45] Mar. 13, 1979

[54] UNIVERSAL SHORT SPINE BOARD SYSTEM

[76] Inventor: Samuel W. Sherman, R.F.D., West Tisbury, Mass. 02575

[21] Appl. No.: 800,707

[22] Filed: May 26, 1977

[51] Int. Cl.² .............................................. A61F 5/04
[52] U.S. Cl. .................................... 128/87 R; 128/134
[58] Field of Search ................ 128/87 R, 87 B, 84 R, 128/82, 133, 134, 75, 78; 5/82; 2/44, 45

[56] References Cited

U.S. PATENT DOCUMENTS

| 954,005 | 4/1910 | Roth | 128/78 |
|---|---|---|---|
| 1,301,276 | 4/1919 | Kroetz | 128/76 |
| 2,489,828 | 11/1949 | Springer | 128/87 R |
| 2,753,864 | 7/1956 | Weidemann, Jr. | 128/87 R |
| 3,315,671 | 4/1967 | Creelman | 128/134 |
| 3,889,668 | 6/1975 | Ochs et al. | 128/134 |

Primary Examiner—John D. Yasko

[57] ABSTRACT

The invention is directed to a universal short spine board system comprising in combination a short spine board and a body conforming vest for immobilization of a patients head, neck, and back and the use of such a system in the performance of emergency medical treatment and subsequent transportation to a further diagnosis and treatment facility.

11 Claims, 3 Drawing Figures

UNIVERSAL SHORT SPINE BOARD SYSTEM

BACKGROUND OF THE INVENTION (1) Field of The Invention

This invention relates to a universal short spine board system for the immobilization of a patient's head, neck and back, and the use of such a spine board system in the performance of emergency medical treatment and transportation.

(2) Description Of The Prior Art

Neck and spinal injuries such as fractures or dislocations of neck vertebrae may occur in a variety of situations, for example, automobile accidents and diving into shallow water. The danger of paralysis is greatest with fractures or dislocations of neck vertebrae, though it is present when other vertebrae are injured. If the spinal chord in the neck is injured, immediate death may result because the nerve supply from the brain to vital organs is shut off. Therefore, fractures of the neck must be handled with utmost caution, keeping the victim absolutely quiet and, if possible, summoning a physician to the scene of the accident. However, in many instances a physician can not be summoned to the scene of an accident, and emergency medical treatment must be given to the patient in anticipation of transporting the patient to a hospital for further diagnosis and treatment. Where transportation is absolutely essential, even for a few feet, it it necessary that, in the case of a neck injury, the person be kept flat on his back, and on a firm frame support.

There are presently available for use by Emergency Medical Teams spine boards and accessories for use in case of cervical and spinal injuries. Those boards of which I am aware comprise either a long or short spine board in combination with a variety of straps by means of which a victim's torso and head are secured to the spine board. Although these various spine boards have been suitable to a certain degree, and are used by a large number of Emergency Medical Teams, there use is attendant with certain disadvantages. Although some of the spine boards available require an inordinant amount of time for application to a victim, e.g., in the seat of an automobile, there are those available provided with special buckles on the straps that can be rather quickly and easily fastened to pins located in openings in the board. Nevertheless, as the straps are the means by which the victim is secured to the spine board, they offer somewhat limited immobility of the patient with respect to the board. This results from the fact that a victim's clothing does not offer good frictional engagement with the spine board and, moreover, because the various straps connecting the victim's body to the spine board do not always conform that well to the contours of the victim's body.

SUMMARY OF THE INVENTION

The invention disclosed herein comprises a universal short spine board system comprising in combination a short spine board and a body conforming vest for immobilization of a victim's head, neck and back to enable the victim to be moved and to be transported to a hospital facility for further diagnosis and treatment.

Quite advantageously, a spine board system in accordance with the invention offers speed in application to a victim not obtainable with use of certain spine boards presently commercially available.

Another advantage with a spine board system in accordance with the invention is that once the spine board is applied to a patient, it provides a greater degree of immobility that heretofor has not been available with presently used spine boards. This results from the fact that a victim's clothing is not in contact with the spine board per se but, instead, is in contact with the body conforming vest of the combination. Thus, greater frictional contact results from the fact that fabric is in contact with fabric, i.e., the fabric of the victim's clothing is in contact with the fabric of the body conforming vest of the combination spine board system. The body conforming vest, moreover, provides for a greater degree of immobilization of a victim on the board in view of the fact that the board is in combination with the vest and the vest readily conforms to the contours of the patient's body.

A further advantage in the use of a spine board system in accordance with the invention is that no metal parts or buckles are involved in the system thereby allowing the patient to be x-rayed while on the spine board more easily and with more satisfactory results.

A still further advantage of a spine board system in accordance with the invention is that such a system more readily fits a wider range of different sizes of individual patients.

In the event of cardiac arrest, moreover, with a spine board system in use in accordance with the invention, cardiopulmonary resuscitation can be more easily performed on a patient.

BRIEF DESCRIPTION OF THE DRAWING

The above and other objects and advantages of the invention will best be understood from the following detailed description of a preferred embodiment thereof, taken in connection with the appended drawings, in which:

FIG. 3 is a perspective view showing the use of a short spine board system in accordance with the invention on a victim in an automobile accident

DETAILED DESCRIPTION OF THE INVENTION AND PREFERRED EMBODIMENTS

Figure 1:
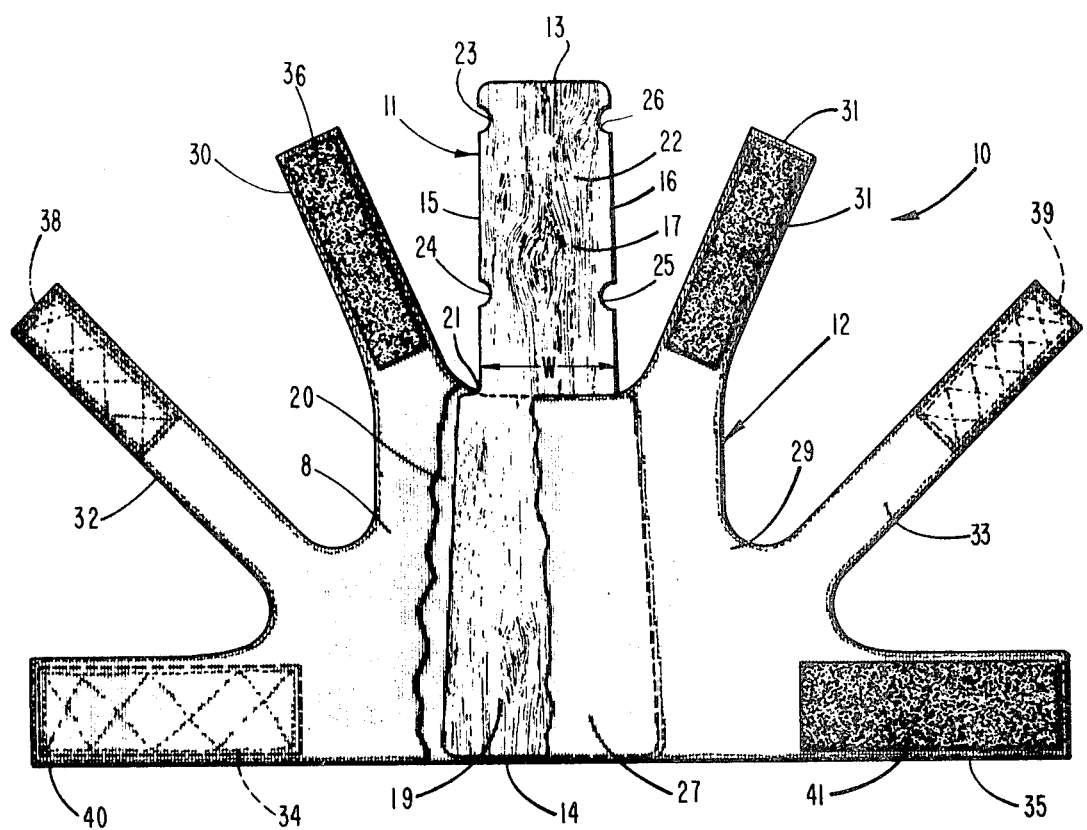
FIG. 1 is a plan view of a short spine board system in accordance with the invention comprising a short spine board and a body conforming vest.

Turning now to the drawing, there is shown therein in FIG. 1, a short spine board system 10 comprising in combination a short spine board 11 and a body conforming vest 12. Short spine board 11 is defined by a top edge 13, a bottom edge 14, two side edges 15, 16, and planar faces 17, 18. The bottom portion 19 of spine board 11 is located as shown, in a pocket 20 provided in the body conforming vest 12, as later described, and which is closed on three sides and is open only at the top for insertion and removal of the spine board, as desired.

As indicated in FIG. 1 of the drawing, spine board 11 is somewhat wider at the bottom edge 14 thereof than at its top edge 13. The width of spine board 11, as shown, narrows gradually from the bottom edge 14 to a point 21 at the mid portion of the spine board where it then abruptly narrows to a width "w", this width being uniform then from the mid portion to the top edge 13 of spine board 11. While this particular configuration of spine board is desirable and provides quite satisfactory performance, it will be appreciated that other, slightly different, configurations can be provided as desired. The spine board can, for example, be of the same width throughout its length. It is highly desireable, however, that the width of the spine board at its widest point, be no greater than about 10 inches, as this generally offers best conformance of the spine board system with the contours of the back of most victims. The spine board should, nevertheless, be wide enough to bridge the hollow of a victim's back so as not to exert undue pressure on the spinal column. While the spine board of the present invention is shown to have planar faces, it will be appreciated that, if desired, these faces can be made somewhat convex-concave in the lower portion of the spine board, if desired. However, such spine boards will be of less universal application due to the differences in body construction.

Spine board 11 is also provided with, in its upper portion 22, along side edges 15, 16, cut outs 23, 24, 25, 26, these being used for a purpose that will later be more fully described. These notches or cut outs, as indicated, are preferably of cresent shape; however, it will be appreciated that other configurations can be provided, if desired. More notches can be provided, if desired, but four have been found satisfactory in the practice of the invention.

Figure 2:
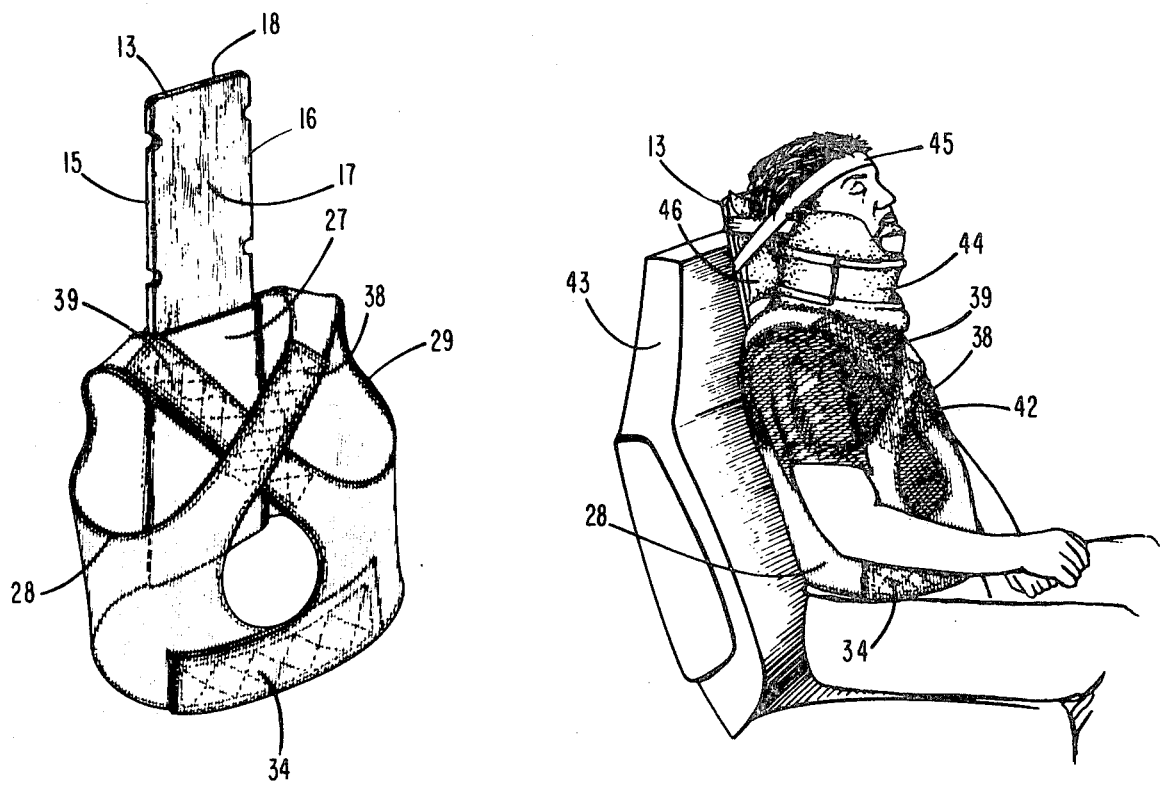
FIG. 2 is a perspective view of a short spine board system in accordance with the invention.

Body conforming vest 12, as indicated more clearly in FIG. 2 of the drawing, comprises a back portion 27 and two side portions 28, 29. These side portions are provided, respectively, with, either on their inside or outside surface as shown, fastening means 36, 37, 38, 39, 40, and 41, which provide ease and speed in fastening and unfastening of the spinal board system. Although in the practice of the invention, strips of hook and pile fasteners such as "Velcro" fasteners have been used, and are quite satisfactory in their performance, it will be appreciated that other fastening means can be used in the practice of the invention. As will be appreciated in reviewing FIGS. 1 and 2 in conjunction, spine board system 10 as shown therein, is so constructed, and the fastening means are so located that it is reversible. This is of tremendous advantage in the application of the spine board system to an accident victim particularly where an accident occurs at night.

Turning now to FIG. 3 of the drawing, there is shown therein a short spine board system 10 in accordance with the invention applied to a victim 42 who has been involved in an automobile accident. As indicated in the drawing, the short spine board system 10 has been inserted between the front of automobile seat 43 and the back of the victim. This is accomplished following the application of a conventional extrication collar 44 applied according to usual techniques. Once the spine board system 10 is inserted and the board properly positioned behind the victim, waist band portions 34, 35 are overlapped and fastened together. Then the shoulder and underarm straps are overlapped and crisscrossed, as shown, and fastened. However, the reverse can be done, if desired, i.e., shoulder straps fastened and then the waist bands. The straps and waist bands should be snug so as to provide a relatively tight, secure fit, and thereby offer maximum immobilization of the victim's body on the spine board. Next the victim's head and neck are made secure to the upper portions of the spine board in the usual fashion by means of head and chin straps 45. Prior to accomplishing this, however, padding 46 should be placed behind the victim's head according to usual techniques. Special straps can be provided for this purpose or, as is commonly done, kling can be used. The patient is then ready to be transferred to a long spine board as is commonly done, for transportation by means of ambulance or the like to a hospital facility for further diagnosis and treatment.

Spine board 11 in accordance with the invention can be manufactured of various materials, for example, wood, plastic, or a light weight metal honeycomb construction. The preferred material of construction is a fine grade plywood such as birch plywood, fine sanded and finished. Metal is less desired as it presents problems in X-ray. The spine board used in the practice of the invention is 10 inches wide at the bottom edge, 8 inches wide at the intermediate portion and 6 inches wide at the upper or top end. It has an overall length of 30 inches and is made of ½ inch birch plywood. Notches for the head and chin straps are provided 1¾ inches and 9½ inches, respectively, from the top edge of the spine board. The notches are of ½ inch radius and are opposite one another in pairs as shown in FIG. 1 of the drawing. The spine board used in the practice of the invention is of the same width from the top edge of the spine board to a point 14 inches from the top edge thereof where it widens at a curved right angle to a width of 8 inches. The width of the spine board then tapers gradually to its maximum width at the bottom edge. All of the corners of the spine board in the practice of the invention are rounded to a ½ inch radius so as to eliminate any sharp corners.

The body conforming vest 12 can be of various materials; however, a closely woven material is preferred so as to limit stretchiness in the body conforming vest. The fabric should be characterized by high strength and preferably be treated so as to be water repellant and mildew resistant. The fabric used in the practice of the invention is a plain weave #8/18oz. cotton chair duck; however, it will be appreciated that other fabrics can be used, provided the characteristics referred to above are met. The Velcro fastener material can be stitched to the vest as desired (e.g., as shown in the drawing) and should be of such a length and width to provide a secure joint. The vest pattern is preferably cut from a base piece of fabric as two separate pieces, and these two pieces then stitched together at their edges and down the back portion between the shoulder straps (not shown) to form a pocket for location of the base portion of the spine board. It will be appreciated that the pocket so formed can be open at only the top, or both ends can be open, as desired. Where two openings are provided, they need not be of the same width, e.g., the spine board is wider at the bottom than at the top, as in FIG. 1. The fabric pieces can be, if desired, so stitched together that the opening at the top of the pocket is only wide enough to allow the upper portion of the board to pass through. Thus, the board is inserted through the wider opening in the bottom of the pocket and is prevented from passing out the top opening by the more narrow width. The bottom opening can be provided with snap fasteners, if desired, so that it can be closed.

In another manner of manufacture, the back and side portions can be cut out as individual pieces and stitched together, as desired, either single or double thickness. To the back portion of the vest, in this case, is stitched a panel wide enough so as to form a pocket for insertion of the spine board. The panel is stitched along its side edges to the back portion and along its bottom edge, or the bottom edge can be left free as desired, as above disclosed. The top edge must be wide enough for insertion of the spine board in the event the bottom edge is stitched. Thus, the spine board can be removed, as desired, and the body conforming vest washed or otherwise made clean.

As many different embodiments of this invention will occur to those skilled in the art, it is to be understood that the specific embodiments of the invention as presented herein are intended by way of illustration only and are not limiting upon the inventon, but that the limitations thereon are to be determined only from the appended claims.

What I claim is:

1. Spine board system capable of reversiblity for use in connection with a patient having a cervical injury comprising in combination a short spine board for positioning against a patient's back of sufficient width to bridge the hollow of the patient's back so as not to exert undue pressure on the patient's spinal column, and having a lower portion for supporting a patient's back and an upper portion for supporting a patient's head and a body conforming vest comprising side portions conforming to said patient's body and, a back portion intermediate said side portions, a pocket in said back portion for containing the spine board during use of the spine board system.

2. Spine board system in accordance with claim 1 wherein the spine board comprises an elongated board of predetermined width and planar front and back surfaces.

3. Spine board system in accordance with claim 2 wherein the width of the lower portion of the spine board is greater than the upper portion.

4. Spine board system in accordance with claim 3 wherein two pairs of opposed notches are provided along the edges of the spine board in said upper portion.

5. Spine board system in accordance with claim 4 wherein the spine board comprises finished birch plywood.

6. Spine board system in accordance with claim 1 wherein the side portions of the body conforming vest each comprises a shoulder strap and an under arm strap and a band for fastening around a victim's waist.

7. Spine board system in accordance with claim 6 wherein the vest comprises a closely woven fabric.

8. Spine board system in accordance with claim 1 wherein the straps and bands are provided with adjustable fastening means.

9. Spine board system in accordance with claim 8 wherein the fastening means are hook and loop type fasteners, and said fastening means are so located on the said straps and waist bands as to provide a reversible spine board system.

10. Spine board system in accordance with claim 1 wherein the pocket is open at the top and bottom thereof for insertion of the spine board and said pocket comprises means for closing the bottom of the pocket.

11. Spine board system in accordance with claim 3 wherein the width of the pocket narrows gradually from its bottom to the top thereof and said spine board is of similar tapering width.

* * * * *